(12) United States Patent
Powers et al.

(10) Patent No.: US 6,360,120 B1
(45) Date of Patent: Mar. 19, 2002

(54) METHOD AND APPARATUS FOR TRANSFERRING PATIENT DATA GENERATED BY AN EXTERNAL DEFIBRILLATOR

(76) Inventors: Daniel J Powers, 2145 Squak Mountain Loop SW., Issaquah, WA (US) 98027; Cecily Anne Snyder, 545 Arguello St. #4, San Francisco, CA (US) 94118

( * ) Notice: Subject to any disclaimer, the term of this patent is extended or adjusted under 35 U.S.C. 154(b) by 0 days.

(21) Appl. No.: 09/417,382

(22) Filed: Oct. 13, 1999

(51) Int. Cl.[7] .............................................. A61B 5/0432
(52) U.S. Cl. ...................................... 600/510; 439/909
(58) Field of Search ................................ 600/510, 522, 600/523; 607/5; 439/909, 620, 894, 946

(56) References Cited

U.S. PATENT DOCUMENTS

| | | | |
|---|---|---|---|
| 5,169,328 A | * 12/1992 | Johnson | ....................... 439/188 |
| 5,607,454 A | 3/1997 | Cameron et al. | |
| 5,735,879 A | 4/1998 | Gliner et al. | |
| 5,836,993 A | 11/1998 | Cole | |
| 5,879,374 A | 3/1999 | Powers et al. | |
| 5,967,817 A | 10/1999 | Greenstein | |
| 6,050,848 A | * 4/2000 | Yao | ............................ 439/483 |
| 6,088,617 A | * 7/2000 | Arand et al. | |
| 5,934,920 A | * 8/2000 | Ito et al. | ...................... 439/159 |

OTHER PUBLICATIONS

Cummins, et al., Improving Survival From Sudden Cardiac Arrest: The "Chain of Survival" Concept Circulation 83:1832–1847 (1991).
The Critical Moment, Newman et al, Early Defibrillation Making Waves Across American JEMS Supplement, S3–S8.

* cited by examiner

*Primary Examiner*—Scott M. Getzow

(57) ABSTRACT

A method and apparatus for transferring patient data recorded by a defibrillator during treatment of a patient. In particular, a recordable memory chip within a medical electrode connector. Further includes a clock associated with the memory also contained within the medical electrode connector. Electrotherapy devices include defibrillators, cardioverters and training devices that simulate the operation of an electrotherapy device. Defibrillators include automatic or semi-automatic external defibrillators (AEDs).

55 Claims, 5 Drawing Sheets

METHOD AND APPARATUS FOR TRANSFERRING PATIENT DATA GENERATED BY AN EXTERNAL DEFIBRILLATOR

BACKGROUND OF THE INVENTION

1. Field of the Invention

This invention relates generally to a method and apparatus for transferring patient data recorded by a defibrillator during treatment of a patient. In particular, this invention relates to providing a recordable memory chip within the electrode connector. Electrotherapy devices include defibrillators, cardioverters and training devices that simulate the operation of an electrotherapy device. Defibrillators include automatic or semi-automatic external defibrillators (AEDs).

2. Description of the Prior Art

Electrotherapy devices are used to provide electric shocks to treat patients for a variety of heart arrhythmias. For example, external defibrillators typically provide relatively high-energy shocks to a patient (as compared to implantable defibrillators), usually through electrodes attached to the patient's torso. External defibrillators are used to convert ventricular fibrillation or shockable tachycardia to a normal sinus rhythm. Similarly, external cardioverters can be used to provide paced shocks to convert atrial fibrillation to a more normal heart rhythm.

In 1991 the Advanced Cardiac Life Support Subcommittee of the American Heart Associate made a report to Health Professionals calling for increased access to defibrillation in order to improve the survival rates from sudden cardiac arrest (SCA). [Cummins, et al. "Improving Survival From Sudden Cardiac Arrest: The 'Chain of Survival' Concept" *Circulation* 83(5): 1832–1847 (1991).] The statistics themselves are staggering. On average 1000 adults die from SCA each day. Over 70% of these deaths occur in the home. Because the survival rate decreases 10% for every minute that passes, unless a defibrillator is available within the first few critical minutes, a victim of SCA has little chance of survival. If defibrillation were available, many of these people would survive. Following the AHA's recommendations, there has been increased awareness of the importance of public access defibrillation and defibrillators have become increasingly available. [See, e.g., Newman, "Early Defibrillation—Making Waves Across America," JEMS Suppl. S4–S8 (January 1997).] The first phase of early defibrillation has been training designated lay responders in proper deployment of a defibrillator. Designated lay responders include, for example, fire fighters, police officers, flight attendants and security guards. However, with 70% of SCA occurring in the home, it becomes increasingly important to design a device that can be deployed by the average citizen in a home emergency.

One problem that could arise as defibrillators become ubiquitous relates to the ability to quickly and easily transfer patient data through the responder tiers. For example, a patient may initially be treated by a first responder carrying an AED. Information may be collected by the defibrillator relating to the patient ECG, shock decisions, etc. Thereafter a second tier responder, such as a paramedic, may arrive to provide treatment. At that time the second tier responder may wish to attach a defibrillator which provides additional functionality. Finally, the patient is transferred to a hospital. At some point it might be desirable to collected the data that was collected by each of the defibrillators in treating the patient to compose a continuous ECG readout. Where each piece of data is collected by a different machine and then correlated, errors could arise, for example, in the time correlation of the data—for example where the clocks of the two devices are not set to the same base time.

What is needed is a method and apparatus for improving the data stream for a patient as he moves from a first tier responder to a second tier responder to a hospital. More specifically, what is needed is a way to provide data collection for the patient which is incorporated into an electrode connector.

SUMMARY OF THE INVENTION

An electrical medical electrode adapter is disclosed comprising: a housing, wherein at least one end of the housing forms a cable connector; an electrical conductor electrically connected to a socket within a shell of the cable connector; and memory disposed within the housing electrically connected to the electrical conductor. Typically the cable connector forms a male end which mates with a female housing end disposed on a defibrillator. In one embodiment, a pair of defibrillator electrodes electrically connected to the housing. Alternatively, a set of monitoring pads electrically connected to the housing. In its simplest form, a plurality of electrode pads are provided. That plurality includes from 2–12 electrodes; typically, three, five or twelve electrode pads. Where the medical electrode adapter is not formed integrally with the electrode pads, a female portion comprising an interior chamber is also provided which is adapted to receive a male medical electrode cable connector. In addition to memory, the adapter may include a clock. The clock would then be used to associate medical event data to be stored on the memory with time. Where a clock is provided a power source would also be provided. The capacity of the memory provided in the adapter should be sufficient to store 20 minutes of ECG sampled at 200 Hz; or approximately 500 kbytes.

A method of deploying a defibrillator is also provided comprising: turning the defibrillator on; attaching electrode pads to a patient; inserting a cable connector associated with the electrode pads into a housing for receiving the cable connector within the defibrillator; recording ECG data to a memory module associated with an electrode adapter associated with the electrode pads; removing the electrode adapter; and retrieving ECG data from the electrode adapter. Additionally, if an advanced tier responder arrives the additional step of disconnecting the electrode adapter from the first defibrillator and attaching the electrode adapter to a second defibrillator, wherein the electrode pads are still attached to the patient. Time data may be associated with patient ECG data using a clock on the electrode adapter associates or a clock associated with each of the defibrillators. In one embodiment, all ECG and event data relating to a medical emergency for a patient is recorded onto the memory. Alternatively, only a selected portion of the ECG data may be recorded. In this instance, optimally, a window of ECG data surrounding an event is recorded. An appropriate window of data is, for example, a twenty second window, i.e., twenty seconds before the event and twenty seconds after the event. Events for which a data window might be appropriate include: shock delivery, shock advised, no shock advised, and heart rate alarm.

BRIEF DESCRIPTION OF THE DRAWINGS

In FIG. 1*a*, the electrode system 36 includes a memory module 32, an electrode adapter 26 and electrodes 28. In FIG. 1*b,* the electrode system 36 also includes a clock 34.

DESCRIPTION OF THE PREFERRED EMBODIMENTS

The following discussion is presented to enable a person skilled in the art to make and use the invention. Various modifications to the preferred embodiment will be readily apparent to those skilled in the art, and the generic principles herein may be applied to other embodiments and applications without departing from the spirit and scope of the present invention as defined by the appended claims. Thus, the present invention is not intended to be limited to the embodiment show, but is to be accorded the widest scope consistent with the principles and features disclosed herein.

Figure 1A:
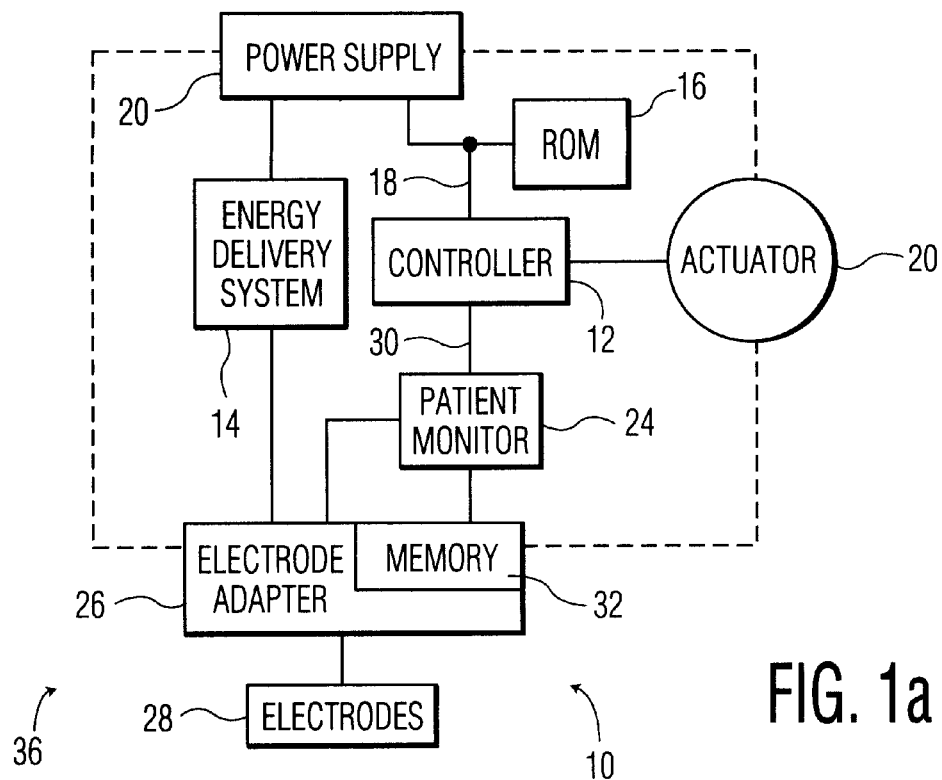
FIGS. 1*a* and 1*b* are block diagrams of an electrotherapy device showing a detachable electrode system.

FIG. 1*a* is a block diagram showing a device 10. Device 10 is an electrotherapy device. The device 10 may be include the ability to defibrillate, cardiovert, or pace a patient, or a combination of these features. Device 10 has a controller 12 that operates an energy delivery system 14 and performs other aspects of the operation of the device. Software instructions for the operation of the device are accessible from read only memory (ROM), such as incorporated ROM 16. The controller accesses instructions for operation from ROM 16. It should be understood that, in this and other embodiments described below, "controller" means a microprocessor, controller, gate array, other control logic, or any combination of these elements.

Controller 12 communicates with ROM 16 via a memory bus 18. A recordable memory module 32 is attached to device 10 via an electrode system 36, as shown in FIG. 1*a.* Electrode system 36 includes electrodes 28 and an electrode adapter 26.

As contemplated by this embodiment, memory module 32 is integral with the electrode adapter 26. Electrode adapter 26 is connected to electrodes 28 and is removably connected to the device 10. A suitable electrode system 36 adaptable for use in this invention would be, for example, Heartstream ForeRunner® electrodes.

Once the electrode adapter 26 is attached to the device 10, memory module 32 communicates with controller 12 over memory bus 30.

Electrodes 28 communicate with a patient monitor 24 via electrode adapter 26 to provide patient ECG data from the patient to the patient monitor 24. Electrodes include electrodes capable of delivering defibrillation, monitoring a patient condition, delivering pacing pulses, or a combination of those features. In an AED, the patient monitor 24 monitors the patient for a heart rhythm and subsequently determines whether the monitored rhythm is shockable. When the rhythm is shockable, the patient monitor 24 then communicates a shock decision to the controller 12. The controller 12, then communicates to the energy delivery system 14. The energy delivery system 14, then delivers a therapeutic energy pulse to the patient (not shown) through electrodes 28 attached to the defibrillator 10 via electrode adapter 26, using the power supply 20 as the energy source.

Figure 2A:
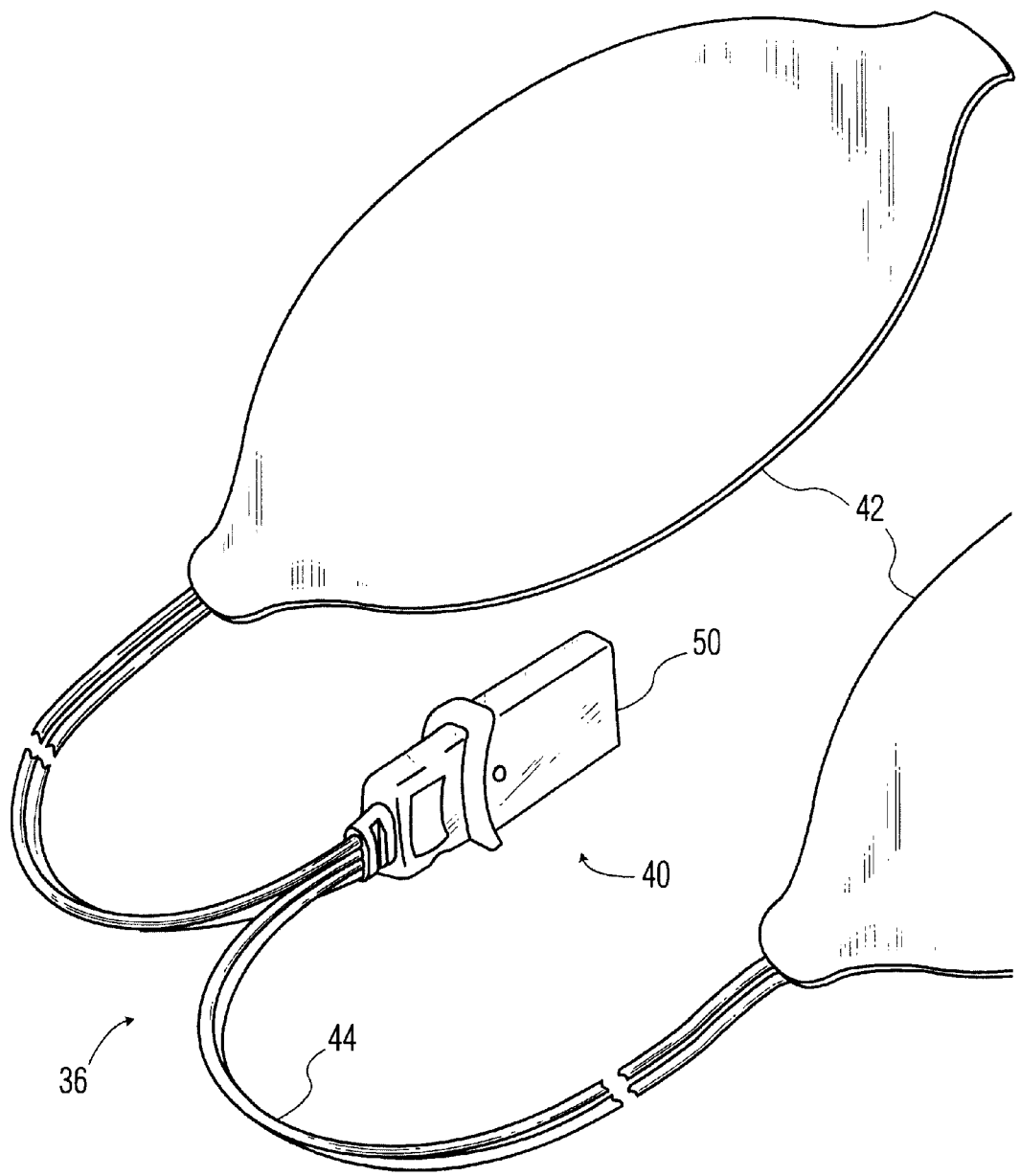
FIG. 2*a* is a perspective drawing of a pair of an electrode system comprising a pair of disposable electrodes integrally formed with an electrode adapter having memory.
Figure 2B:
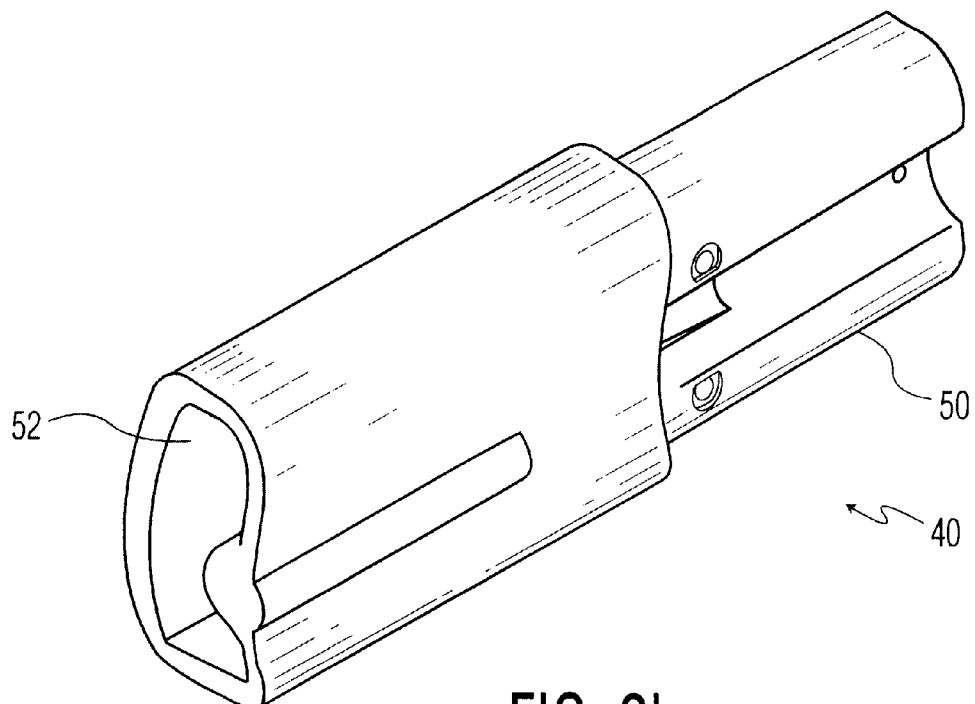
FIG. 2*b* is a perspective drawing of an electrode adapter having memory for use in connection with a defibrillator and a pair of disposable electrodes.
Figure 2C:
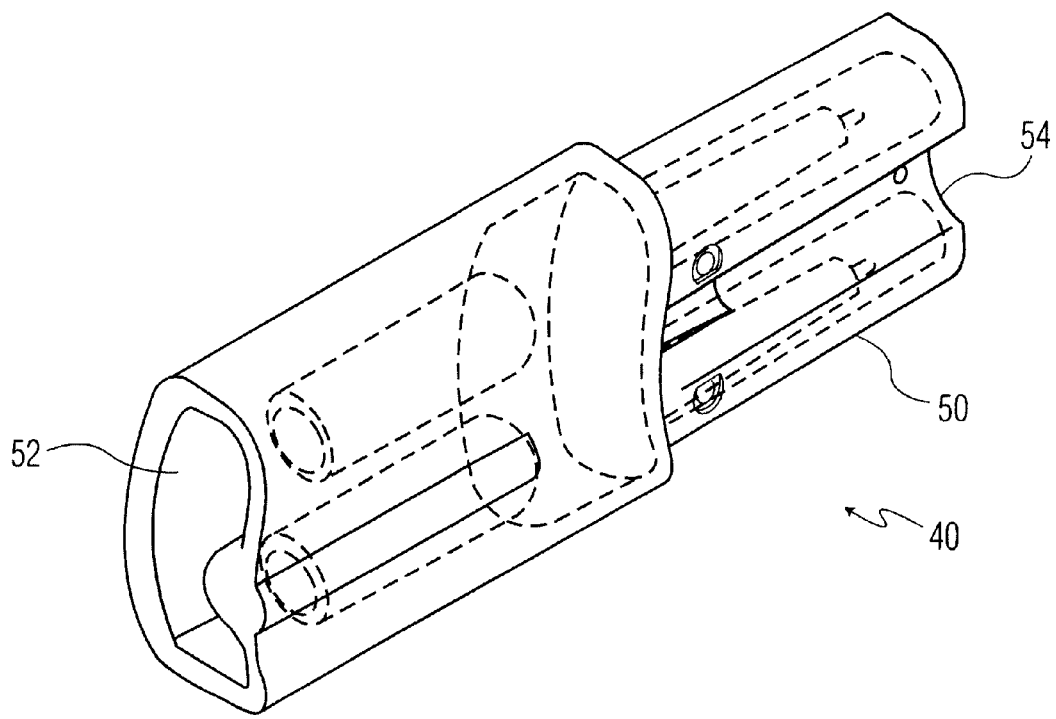
FIG. 2*c* is a perspective drawing of an electrode adapter having memory for use in connection with a defibrillator and a pair of disposable electrodes showing the interior portions of the male and female ends of the adapter.

Data collected during the patient treatment event is stored on the memory module 32 associated with the electrode connector (shown in FIGS. 2*a*–2*c*). The data collected includes, for example, full ECG data along with shock decisions, and shock deliveries. Where full ECG data is recorded, the memory module should have the capacity to record, for example, 20 minutes of ECG data which is sampled, for example, at the rate of 200 Hz. A suitable amount of memory in this instance would be approximately 500 kbytes. In another alternative, the data collected can be shortened so that it includes the ECG data for a window surrounding shock delivery (for example, 5 seconds before and after delivery of a shock). In this situation substantially less memory can be used. Or, data collected may just be a summary of the events, for example:

Defibrillator Turned On

VF Detected

Shock Advised

No Shock Advised

Shock Delivered

Normal Sinus Rhythm

Heart rate alarm condition

In this scenario even less memory would be required.

Figure 1B:
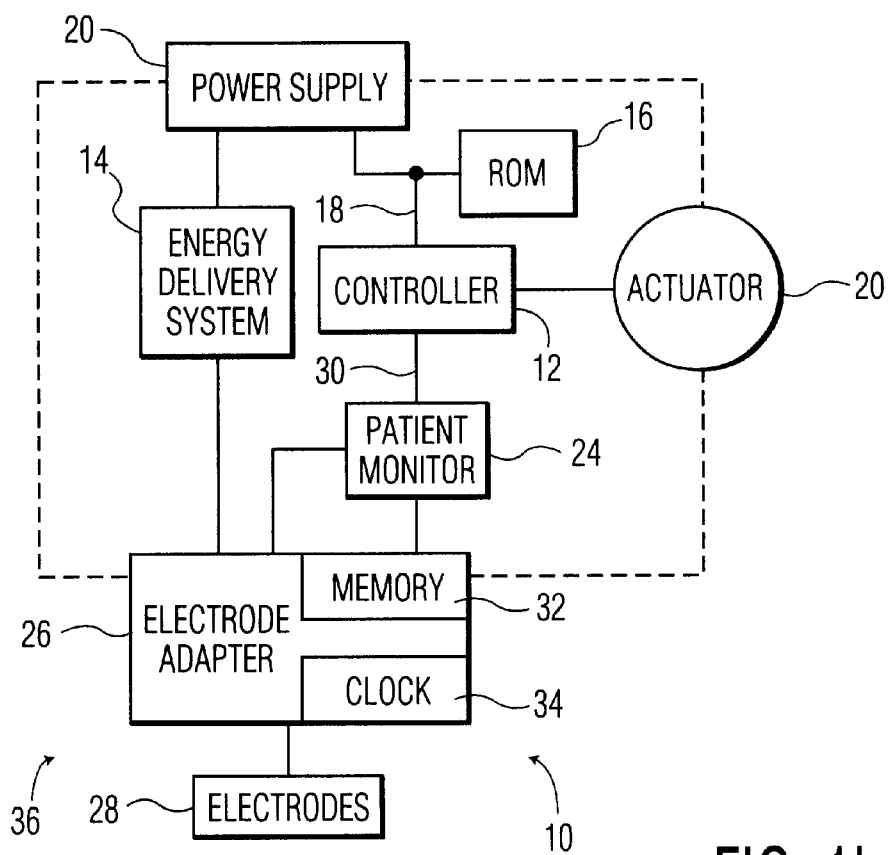

In an alternative embodiment shown in FIG. 1*b,* a clock 34 is included in the electrode adapter 26 in communication with the memory module 32. Thus, when the defibrillator collects data it can associate the time of the adapter clock with the data. By providing clock information in conjunction with the memory module 32 any deviations that might have occurred from collecting data, which includes time data from defibrillators having clocks set to separate times, would not result, and a more accurate data stream from the patient would be obtained. Where the clock 34 is incorporated in the electrode adapter 26, a power source (not shown) would be provided to power the clock 34. A suitable clock would be, for example a DS1306 available from Dallas Semiconductors (www.dalsemi.com), suitable power sources for the clock include, for example, Li coin batteries.

Turning to FIG. 2*a,* electrode system 36 comprises an electrode connector housing 40 for connecting the electrode system 36 to device. In this embodiment, the housing comprises a cable connector 50. The cable connector 50 has one ore more electrical conductors electrically connected to corresponding sockets within a shell. A pair of electrodes 42 is connected to the housing 40 via wires 44. A memory module 32 (FIGS. 1*a* and 1*b*) is included within the housing 40 for connection to the device. Memory module 32 is configured so that it is electrically connected to the device. For purposes of illustration, FIG. 2*a* has been depicted showing two electrodes. However, it will be appreciated by those of skill in the art that a plurality of electrodes can be used. For example, from 2–12 electrodes are appropriate for use in monitoring patient ECG. Additional information on electrode connector construction can be found in U.S. Pat. No. 5,967,817 by Greenstein entitled "Medical Connector Apparatus," the disclosure of which is incorporated herein.

As discussed above with respect to FIG. 1*b,* a clock 32 and corresponding power supply may also be provided within housing 40. The actual configuration of the memory module, clock and power supply is not disclosed in order to avoid obscuring the invention. However, suitable configurations are known by those skilled in the art.

Turning now to FIG. 2b, the housing 40 of the electrode adapter shown in FIG. 2a has been modified so that in addition to providing a cable connector 50, it also is adapted to receive a mating cable connector on one end. Thus, one end forms an interior chamber 52 for receiving a mating cable connector. Electrical conductors electrically connected to sockets within a shell are located within the interior chamber 52 such then when a mating cable connector is inserted into the interior chamber of the adapter it makes electrical contact between the mating cable connector and housing 40. In this embodiment, the adapter is configured so that it is removable from the electrode pads and the defibrillator and thus is reusable. The advantage of this configuration is that it allows data to be collected without removing the electrode pads from the patient. A caregiver need only disconnect the adapter from the electrode connector and then reconnect the electrode connector to the defibrillator or to another adapter prior to reconnecting to another defibrillator.

FIG. 2c illustrates the adapter set-up shown in FIG. 2b with the interior portions outlined. As illustrated, the interior female chamber 52 houses two connectors with female chambers. The connectors are adapted to slide over male conductors in a corresponding electrode adapter. The male cable connector end 54 has two female chambers each of which contains a male conductor. When the male cable connector end 54 is inserted into a corresponding female chamber (for example, in a defibrillator housing, not shown), the male cable connector end 54 slides into the corresponding female chamber while the two connectors with female chambers within the female chamber 52 slide over the male conductors of a male cable connector (not shown).

Figure 3:
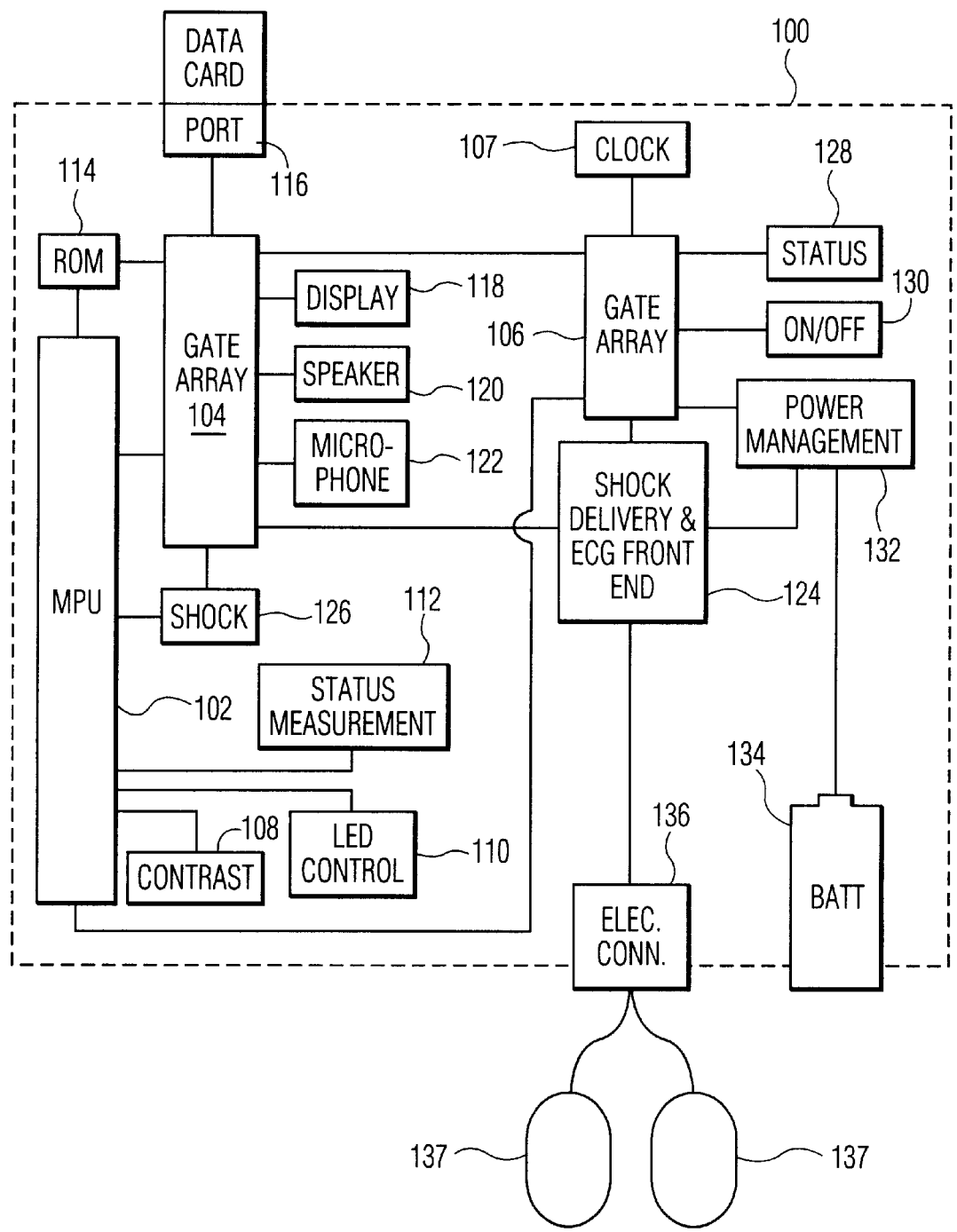
FIG. 3 shows the major components of a semi-automatic external defibrillator in block diagram form.

The major components of an AED are shown in FIG. 3 in block diagram form. Further detailed information about the operation of an AED can be obtained in U.S. Pat. No. 5,836,993, to Cole for "Electrotherapy Device Control System and Method," the specification of which is incorporated herein. As will be appreciated by those of skill in the art, the invention can be used in a variety of AEDs and is not limited to this configuration, which is used for illustration purposes only.

In this illustration, defibrillator control functions are divided among a microprocessor unit (MPU) 102 and two custom gate arrays 104 and 106.

MPU 102 performs program steps according to software instructions provided to it from ROM 114. MPU 102 controls the operation of certain buttons (such as display contrast buttons 108) and certain system LED's 110 (such as LED's associated with the shock button and the electrode connector). MPU 102 also receives system status information as shown by block 112.

Gate array 104 implements the memory map to system ROM 114. System ROM 114 is preferably flash ROM, although EPROM or any other electrically erasable and programmable nonvolatile memory could be used. Gate array 104 also controls a display 118, a speaker 120, and a microphone 122. Gate array 104 can actuate a relay within the shock delivery and ECG front-end system 124 in response to actuation of a shock button 126 by a user during treatment mode.

Gate array 106 provides a system monitor function by performing automatic self-tests of the defibrillator and its components. The gate array 106 displays the operational status of the defibrillator on a status display 128. Details of suitable self-tests may be found in U.S. Pat. No. 5,879,374, to Powers, et al. for "External Defibrillator with Automated Self-Testing Prior to Use," the specification of which is incorporated herein by reference. Gate array 106 is also the defibrillator's interface with a user-activated on/off switch 130. Gate array 106 controls the power management subsystem 132 to provide power to operate system components from power supply 134 and to provide energy to the shock delivery system's capacitor(s) for a therapeutic shock during treatment mode. Gate array 106 also interfaces with the defibrillator's ECG front end, enables the shock delivery system to deliver a shock in response to detection of a patient ECG pattern requiring treatment (and actuation of the shock button), and controls delivery of the shock to electrode connector 136 in response to shock delivery status information obtained during delivery of the shock. Further information regarding this last function may be found in U.S. Pat. No. 5,735,879 to Gliner et al. for "Electrotherapy Method for External Defibrillators," and U.S. Pat. No. 5,607,454, to Cameron et al. for "Electrotherapy Method and Apparatus," the specifications of which are incorporated herein.

These defibrillator components communicate with each other over suitable communication buses, as shown.

External defibrillator 100 can be operated in different modes, such as self-test mode, stand-by mode, set-up mode, patient treatment mode, training mode and code-transfer mode. The operational characteristics of defibrillator 100 differ in each mode. In addition, the operational characteristics of the defibrillator in any one of the modes can be changed as explained below.

Operation of the external defibrillator of this embodiment commences with the insertion of a power supply 134 or user activation of the power on button. Once gate array 106 confirms that a power supply 134 is inserted, gate array 104 prompts MPU 102 to begin its boot sequence. The boot sequence begins with MPU 102 sending out a series of addresses to power supply 134.

As is known in the art, while in patient treatment mode, the defibrillator 100 typically (1) determines whether electrodes 137 are attached to electrode connector 136; (2) receives ECG information from a patient through such electrodes; (3) analyzes the ECG information to determine whether a therapeutic shock is advised; and (4) delivers a shock to the patient through the electrodes 137 if a shock is advised and if the shock button 126 is actuated by a user.

Figure 4:
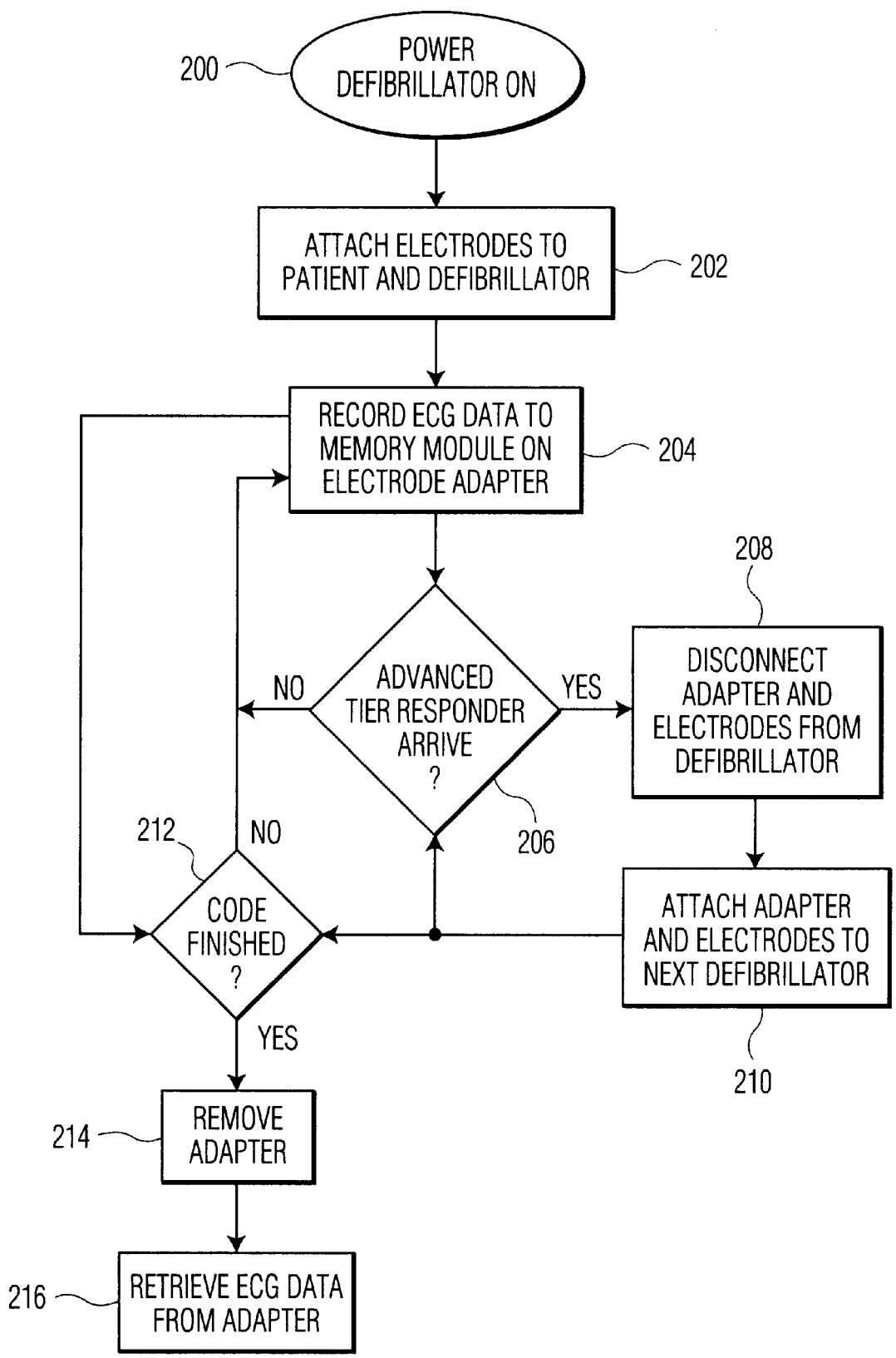
FIG. 4 is a flow chart showing the method of operating the electrotherapy device according to the invention.

Turning to FIG. 4, the method of deploying the invention is shown. Initially, the first responder defibrillator is powered up 200. After powering the defibrillator, electrode pads are attached to the patient 202. The attached defibrillator then begins to receive ECG information from the patient through the attached electrode pads. The ECG information is stored on the memory module associated with the electrode adapter (either as full ECG data or selected data as described above) 204. If an advanced tier responder arrives 206 the adapter is then disconnected 208 from the defibrillator it was attached to in step 202. The adapter is then attached to the advanced tier responder defibrillator 210. In the event an advanced tier responder has not arrived, then the defibrillator continues to record ECG data received from the first tier defibrillator to the memory module in the adapter. Once the code is finished 212, then the adapter is removed 214 and the ECG data recorded onto the adapter is retrieved 216 for use by the advanced caregivers (such as physicians at the hospital).

As discussed above, other modifications falling within the scope of this invention will be apparent to persons of skill in the art. Thus, the invention is not to be limited by the specification, but interpreted according to claims that follow.

What is claimed:

1. An electrical medical electrode adapter comprising:
a housing operable to electrically connect to an electrode pad, wherein at least one end of the housing forms a cable connector;
an electrical conductor electrically connected to a socket within a shell of the cable connector; and
memory disposed within the housing electrically connected to the electrical conductor.

2. The electrical medical electrode adapter of claim 1 further comprising an interior chamber adapted to receive a medical electrode cable connector.

3. The electrical medical electrode adapter of claim 2 further comprising a power source in communication with the clock.

4. The electrical medical electrode adapter of claim 1 further comprising a clock in communication with the memory.

5. The electrical medical electrode adapter of claim 1 wherein the memory is sufficient to store 20 minutes of ECG sampled at 200 Hz.

6. The electrical medical electrode adapter of claim 1 wherein the memory is a 500 kbyte memory.

7. An electrical medical electrode adapter comprising:
a housing, wherein at least one end of the housing forms a cable connector;
an electrical conductor electrically connected to a socket within a shell of the cable connector;
memory disposed within the housing electrically connected to the electrical conductor; and
a pair of defibrillator electrode pads electrically connected to the housing.

8. An electrical medical electrode adapter comprising:
a housing, wherein at least one end of the housing forms a cable connector;
an electrical conductor electrically connected to a socket within a shell of the cable connector;
memory disposed within the housing electrically connected to the electrical conductor; and
a set of monitoring electrode pads electrically connected to the housing.

9. An electrical medical electrode adapter comprising:
a housing, wherein at least one end of the housing forms a cable connector;
an electrical conductor electrically connected to a socket within a shell of the cable connector;
memory disposed within the housing electrically connected to the electrical conductor; and
a plurality of electrode pads electrically connected to the housing.

10. The electrical medical electrode adapter of claim 9 wherein three electrode pads are provided.

11. The electrical medical electrode adapter of claim 9 wherein five electrode pads are provided.

12. The electrical medical electrode adapter of claim 9 wherein twelve electrode pads are provided.

13. A method of deploying a defibrillator comprising:
turning the defibrillator on;
attaching electrode pads to a patient;
inserting a cable connector associated with the electrode pads into a housing for receiving the cable connector within the defibrillator;
recording ECG data to a memory module associated with an electrode adapter associated with the electrode pads;
removing the electrode adapter; and
retrieving ECG data from the electrode adapter.

14. The method of claim 13 further comprising the step of:
if an advanced tier responder arrives, disconnecting the electrode adapter from the first defibrillator and attaching the electrode adapter to a second defibrillator, wherein the electrode pads are still attached to the patient.

15. The method of claim 13 wherein a clock within the electrode adapter associates a time with data recorded from the defibrillator.

16. The method of claim 15 wherein the clock associated with the adapter associates time information with the ECG data received from the patient.

17. The method of claim 13 wherein all the ECG data relating to a medical emergency for a patient is recorded.

18. The method of claim 13 wherein a selected portion of the ECG data relating to a medical emergency for a patient is recorded.

19. The method of claim 18 wherein the selected portion of ECG data is a window of ECG data surrounding an event.

20. The method of claim 19 wherein the window of ECG data is a twenty second window.

21. The method of claim 19 wherein the event is selected from the group consisting of: shock delivery, shock advised, no shock advised, and heart rate alarm.

22. An adapter, comprising:
a housing;
an electrical conductor disposed within the housing and operable to connect to a medical device; and
a memory disposed within the housing and connected to the electrical conductor.

23. The adapter of claim 22 wherein the memory is operable to receive data via the conductor.

24. The adapter of claim 22 wherein the memory is operable to receive data from the medical device via the conductor.

25. The adapter of claim 22 wherein the electrical conductor is operable to connect to an electrode pad.

26. The adapter of claim 22 wherein the electrical conductor is operable to connect to a defibrillator.

27. A module, comprising:
a housing operable to connect to a first medical device and to a second medical device and to couple the first medical device to the second medical device; and
a memory disposed in the housing and operable to be coupled to one of the first and second medical devices.

28. The module of claim 27 wherein:
the housing is operable to connect to a defibrillator; and
the memory is operable to communicate with the defibrillator.

29. The module of claim 27 wherein the memory is operable to receive data from the one of the first and second medical devices.

30. The module of claim 27 wherein the memory is operable to communicate with the first and second medical devices.

31. The module of claim 27, further comprising a clock disposed in the housing and coupled to the memory.

32. A module, comprising:
a housing operable to connect to a first medical device and to a second medical device; and
a memory disposed in the housing and operable to be coupled to and to provide data to one of the first and second medical devices.

33. A module, comprising:
a housing having first and second connectors respectively operable to couple to first and second medical devices; and
a memory disposed within the housing, coupled to one of the first and second connectors, and operable to provide data to the one of the first and second medical devices.

34. The module of claim 33 wherein the memory is operable to receive data from the one of the first and second medical devices.

35. The module of claim 33 wherein the memory is coupled to the first and second connectors.

36. The module of claim 33, further comprising a clock disposed in the housing and coupled to the memory device.

37. A module, comprising:
a housing having first and second connectors respectively operable to couple to first and second medical devices; and
a memory disposed within the housing, coupled to the first and second connectors, and operable to receive data from the first and second medical devices.

38. A pad assembly, comprising:
a pad;
a memory; and
a conductor that tethers the memory to the pad.

39. The assembly of claim 38 wherein the pad comprises a defibrillator-electrode pad.

40. The assembly of claim 38 wherein the pad comprises a monitor pad.

41. The assembly of claim 38, further comprising a clock tethered to the pad by the conductor and coupled to the memory.

42. The assembly of claim 38, further comprising a connector tethered to the pad by the conductor and operable to couple the memory to a medical device.

43. The assembly of claim 38, further comprising a connector tethered to the pad by the conductor and operable to couple the memory and the pad to a medical device.

44. A system, comprising:
first and second medical devices; and
a module operable to couple the first medical device to the second medical device, the module including a memory operable to communicate with one of the first and second medical devices.

45. The system of claim 44 wherein:
the first medical device comprises a pad; and
the second medical device comprises a defibrillator.

46. The system of claim 44 wherein:
the first medical device comprises a pad;
the second medical device comprises a defibrillator; and
the memory is operable to store data from the defibrillator.

47. The system of claim 44 wherein:
the first medical device comprises a pad;
the second medical device comprises a defibrillator; and
the memory is operable to provide stored data to the defibrillator.

48. The system of claim 44 wherein:
the module comprises a housing; and
the memory is disposed within the housing.

49. The system of claim 44 wherein:
the module includes a housing;
the module includes a clock disposed within the housing and coupled to the memory; and
the memory is disposed within the housing.

50. A method, comprising:
coupling a pad connector to a medical device;
storing data from the medical device in a memory that is disposed in the pad connector;
uncoupling the pad connector from the medical device; and
retrieving the stored data from the memory.

51. The method of claim 50 wherein:
coupling comprises coupling the pad connector to a defibrillator; and
storing comprises storing data from the defibrillator in the memory.

52. A method, comprising:
storing first data from a first medical device in a memory;
uncoupling the memory from the first medical device;
coupling the memory to a second medical device;
storing second data from the second medical device in the memory; and
retrieving the first and second data from the memory.

53. The method of claim 52, further comprising uncoupling the memory from the second medical device before retrieving the first and second data.

54. The method of claim 52, further comprising coupling the memory to the first medical device before storing the first data.

55. A method, comprising:
storing first data from a first defibrillator in a memory;
uncoupling the memory from the first defibrillator;
coupling the memory to a second defibrillator;
storing second data from the second defibrillator in the memory; and
retrieving the first and second data from the memory.

* * * * *